United States Patent
Luedemann

(10) Patent No.: US 10,094,695 B2
(45) Date of Patent: Oct. 9, 2018

(54) INTERFEROMETRIC MEASUREMENT OF LIQUID VOLUMES

(71) Applicant: Hans-Christian Luedemann, Bolton, MA (US)

(72) Inventor: Hans-Christian Luedemann, Bolton, MA (US)

( * ) Notice: Subject to any disclaimer, the term of this patent is extended or adjusted under 35 U.S.C. 154(b) by 0 days.

(21) Appl. No.: 15/422,757

(22) Filed: Feb. 2, 2017

(65) Prior Publication Data
US 2017/0205270 A1 Jul. 20, 2017

Related U.S. Application Data

(63) Continuation of application No. PCT/US2015/043910, filed on Aug. 6, 2015.

(60) Provisional application No. 62/036,142, filed on Aug. 12, 2014.

(51) Int. Cl.
*G01B 9/02* (2006.01)
*G01F 23/292* (2006.01)

(52) U.S. Cl.
CPC ......... *G01F 23/292* (2013.01); *G01B 9/0209* (2013.01)

(58) Field of Classification Search
CPC .......................... G01F 23/292; G01B 9/0209
See application file for complete search history.

(56) References Cited

U.S. PATENT DOCUMENTS

| | | |
|---|---|---|
| 5,323,229 A | 6/1994 | May et al. |
| 6,552,806 B1 | 4/2003 | Swinford et al. |
| 6,847,453 B2 | 1/2005 | Bush |
| 6,958,816 B1 | 10/2005 | Dogariu et al. |
| 7,187,455 B2 | 3/2007 | Curtis |
| 7,233,391 B2 | 6/2007 | Schermer et al. |
| 8,934,104 B2 | 1/2015 | Koerner et al. |
| 9,239,226 B2 * | 1/2016 | Fedosejevs ........ G01B 11/0625 |
| 2008/0180694 A1 | 7/2008 | de Groot et al. |

(Continued)

OTHER PUBLICATIONS

The International Preliminary Report on Patentability completed on May 11, 2017 for PCT Application No. PCT/US15/43910.

(Continued)

*Primary Examiner* — Jonathan Hansen
(74) *Attorney, Agent, or Firm* — Brian M. Dingman; Dingman IP Law, PC

(57) ABSTRACT

An apparatus and method for the accurate and non-invasive measurement of the volume of liquid samples by optical interferometry. Small volumes of liquid samples are often contained in and partially fill the wells of a microplate. A low-coherence interferometric ranging system is used to determine the topography of the sample surface exposed by each well. The surface topography, together with the measured, or otherwise known, dimensions of the well, determine the volume of the liquid sample. Embodiment options include confining the optical beams of the interferometer to optical fiber and varying the optical-path length by piezoelectric stretching of a portion of the fiber. Other embodiment options include automation of data collection by stepping the microplate beneath the interferometer, pixelating the optical beam of the interferometer and scanning the microplate by scanning the sample beam of the interferometer with a mirror. Uniformity of the microplate wells is not required.

20 Claims, 5 Drawing Sheets

(56) References Cited

U.S. PATENT DOCUMENTS

2010/0094576 A1 4/2010 de Boer et al.
2014/0267695 A1* 9/2014 Scordato ................ G01F 22/00
                                                          348/135

OTHER PUBLICATIONS

The International Search Report and the Written Opinion dated Apr. 19, 2016 for PCT Application No. PCT/US15/43910.

* cited by examiner

INTERFEROMETRIC MEASUREMENT OF LIQUID VOLUMES

CROSS REFERENCE TO RELATED APPLICATIONS

This application is a continuation of application PCT/US2015/043,910, filed on Aug. 6, 2015, which claimed priority to U.S. Provisional patent application 62/036,142 filed on Aug. 12, 2014. The entire disclosures of both applications are incorporated herein by reference.

BACKGROUND

Field

This invention relates in general to the measurement of liquid-sample volumes and, more specifically, to the use of low-coherence optical interferometry toward that end.

Description of Related Art

In a typical laboratory setting, several small reaction vessels are arranged in a rectangular microplate. These microplates have standardized, common outer dimensions and contain a varying number of vessels, which are referred to as wells. The most common cases are 96, 384, and 1536 wells. The volume of the individual well decreases as the well density of the plate increases. Standardized microplates allow for the use of automated liquid delivery and analysis devices. In many real-world examples, an automatic liquid delivery device is programmed to add specific volumes of various liquids to each of the reaction vessels or wells in a microplate. Subsequently, an automatic analysis device interrogates each of the wells and measures one or several physical or chemical properties. One common example is to read the optical absorbance or emitted fluorescence from each well with a plate reader, but many other measurements are carried out in practice.

In this type of experiment, researchers often derive their knowledge of the volume of liquid added to each well from the instructions sent to the liquid delivery device. Specifically, they rely on the liquid delivery device to add a volume to the well that matches the desired volume as closely as possible. It is, therefore, useful to provide a device whose use enables the independent verification of the performance of the liquid delivery device. In particular, it is useful to provide a device whose use enables the user to independently verify by how much the actually dispensed volume differs from the desired dispense volume. This property is called the accuracy of the liquid delivery device. Similarly, it is important that for the same desired dispense volume, the actual dispense volume exhibit little variation. This property is called the precision of the liquid delivery device.

In practice, automated liquid delivery devices provide for a set of instrument parameters that can be adjusted by the user to ensure that desired dispense volume and actual dispense volume match. Configuring a liquid delivery device for a given experiment by adjusting this set of parameters to ensure accuracy and precision of the liquid delivery device for the specific liquids used in that experiment is one of the most important tasks in reducing the contribution of the liquid delivery device to experimental errors. Typically, a specific set of values has to be chosen for these instrument parameters for each kind of liquid that is being dispensed. Hence, a common industry term for this set of parameters is "liquid class". Often, instrument parameters also have to be adjusted for dispensing different volume ranges.

The optimal values for this set of instrument parameters may vary from liquid to liquid. This is a result of the physical and chemical properties of the liquid and the configuration of those parts of the liquid delivery instrument the liquid is in contact with. Examples for important aspects of the configuration are pipet and tubing wall materials and dimensions as well as dispense speeds. Among the properties of the liquid that come into play are its surface tension, which describes the interaction with the gas above the liquid, and the interfacial tensions, which describe the interaction with solid materials the liquid comes in contact with. The viscosity of the liquid and the temperature also play an important role.

Currently, researchers use various approaches to verify the performance of liquid delivery devices.

Gravimetric Method for Liquid Volume Measurement

In the gravimetric method, the vessel or microplate is weighed on an analytical balance before and after the sample liquid is dispensed. If the density of the liquid is known, the dispensed volume can then be calculated from the difference in weight.

If this method is to be applied to assessing the errors in liquid delivery into individual wells, a weighing step is performed after each dispense operation, which renders the method very time consuming. In this instance, the change in weight to be measured is also rather small, so that static electricity, drafts, and vibrations, for example, may introduce substantial errors to the measurement.

An alternative common practice is weighing the entire plate before and after liquid is dispensed into each of the wells. This measurement yields information about the mean volume dispensed, but does not offer any information about the precision i.e. the well-to-well variability of the dispensed volume.

Photometric Method for Liquid Volume Measurement

In photometric methods, a liquid solution containing a dye at a known concentration and with known absorbance properties is used as the sample liquid. The measured optical absorbance can then be related to the optical path length in the dye solution, which is equal to the liquid fill height of the well. If the dimensions and shape of the well are known, the liquid volume can then be calculated. This method is limited by the accuracy with which typical absorbance plate readers determine sample absorbance.

A variant of the photometric method, ratiometric photometry is described in U.S. Pat. No. 7,187,455 B2. A system using this approach is currently being manufactured and distributed by Artel of Westbrook, Me. This method involves the use of two different solutions of two different dyes, which aids in obviating some of the limitations of a photometric method based on a single dye. The two different dyes are chosen such that their absorption maxima occur at different wavelengths, so that the absorbance of both dyes can easily be measured simultaneously. The method consists of using a dedicated microplate reader attached to a computer with software to analyze small volumes of pre-calibrated, well-characterized dye solutions that were dispensed into pre-calibrated microplates.

For volume measurements, it is important to take into account the shape of the interface between the liquid sample and the gas above it, its meniscus. In an idealized form, it is assumed to be planar and horizontal. However, in a large proportion of cases of practical relevance, the liquid meniscus is not planar. This deviation from planarity is caused by cohesive and adhesive forces between the liquid molecules, between the liquid and the walls of the vessel, and between the liquid and the gas above it.

Accounting for the shape of this meniscus, however, is useful to increase the accuracy of the liquid volume measurement. If the meniscus is curved, measuring the liquid fill height at one point in the well is no longer sufficient to determine the volume of the liquid. Importantly, the shape of the meniscus may vary with the composition of the liquid and the material of the microplate. In the ratiometric photometry method described in U.S. Pat. No. 7,187,455 B2 the user is limited to specific liquids that have undergone extensive characterization. In practice, the user purchases these solutions from the manufacturer. U.S. Pat. No. 7,187,455 B2 states that these liquids are composed in such a way as to ensure that the meniscus remains very close to planar to ensure the shape of the meniscus does not introduce unacceptably large errors into the volume measurement.

In cases where a user wants to rapidly verify the level of accuracy and precision for a given experimental liquid and the liquid class parameters chosen for this specific experiment, the method described in U.S. Pat. No. 7,187,455 B2 does not provide a convenient solution. Examples for cases such as this are liquids that contain detergents, plasma, or organic solvents, among others.

Further, the method described in U.S. Pat. No. 7,187,455 B2 does not provide a convenient solution for a user who wants to measure the volume of liquid in a plate and then subsequently use that same liquid in an unaltered state for an experiment. The presence of dyes in this method makes this impossible.

Ultrasonic Ranging for Liquid Volume Measurement

A number of commercially available instruments use ultrasonic ranging to sense the elevation of the liquid meniscus. Instruments of this type are the BeeSure manufactured by Bionex Solutions Inc. of Sunnyvale, Calif., and the VolumeCheck 100 by BioMicroLab of Concord, Calif. In one embodiment, a transducer is moved above the well. A pulse of ultrasonic energy is directed toward the surface of the liquid. A fraction of the ultrasonic energy is reflected towards the transducer, where the time of its arrival is measured. The time-of-flight between when the original pulse leaves the transducer and when the reflected pulse impinges on it is related to the distance traversed and the speed of sound in the gaseous medium above the liquid. Upon proper calibration, measuring this time can, therefore, yield the elevation of the meniscus in the well, which in turn is related to the liquid volume contained in the well. Due to inherent limitations in the distance resolution of ultrasound measurements, this method is suitable to detect the presence of liquid in a well, but the resolution is not high enough to measure liquid volumes with sufficient resolution for the needs of many liquid delivery applications. Further, methods relying on ultrasound focus the sensing ultrasonic wavefront into the well of a microplate. For small wells, the ultrasonic wavefront suffers diffraction at the opening of the well, and depth information cannot be recovered from the reflection. This also limits the usefulness of this method for microplates with smaller wells at higher density.

Ultrasonic Ranging in Instruments for Acoustic Liquid Transfer

In another type of commercially available instrument, ultrasonic energy is focused through the bottom of the well. The main purpose of this type of instrument is the transfer of very small droplets of liquid from one microplate into another microplate. As a side product of pursuing this objective, these instruments can also provide a measurement of the liquid fill height. Instruments of this type are manufactured by Labcyte Inc. of Sunnyvale, Calif. and by EDC Biosystems of Fremont, Calif.

In these instruments, a transducer is acoustically coupled to the bottom of the microplate with a water jet. A pulse of ultrasonic energy is triggered and travels through the plate and the liquid until it is reflected at the underside of the liquid meniscus, the liquid-air interface. It then travels back through the liquid and the plate to the transducer, where its arrival is recorded. Given the speed of sound in the liquid, the fill height of the liquid in the well can be determined from the time-of-flight between when the pulse left the transducer and when its reflection impinges upon it.

The utility of this method for routine calibration is limited because the liquid delivery device is very expensive and requires plates of a specific material. Its resolution is limited by the inherent resolution limit of ultrasonic ranging.

Seal-and-Pressurize Method for Liquid Volume Measurement

In another commercially available method, the individual wells of the microplate are connected to individual gas reservoirs of adjustable volume such as syringe-like devices in such a manner that they are sealed by a gasket. An instrument of this type is manufactured by Stratec Biomedical AG of Birkenfeld, Germany. In a sealed chamber such as this which cannot exchange gas with the outside, the pressure of the gas is related to the volume of the chamber by a known relationship. As the volume in the newly connected outside reservoir is reduced, the pressure in the sealed chamber, therefore, rises. Because the liquid is incompressible, knowledge of the change in pressure for a given change in volume, therefore, allows for the determination of the gas volume in the well. By definition, the proportion of the total well volume that is not taken up by gas is taken up by liquid, and the volume of liquid in the well can thus be determined.

Challenges that limit the utility of this method in a laboratory setting include the fact that the gas pressure in the sealed chamber also depends on the temperature. Unless temperature is carefully controlled, it is a major error source.

Second, sealing each well of the plate to its corresponding piston is accomplished by a gasket that touches the top rim of the well, which bears the risk of contamination of the contents of the well.

Fluorescent Dye Method for Liquid Volume Measurement

Another method used by practitioners consists of dispensing a solution of a fluorescent compound. Each well can then be read with a plate reader to determine the amount of fluorescence emitted and thus the amount of liquid dispensed into the well. Measurements of this type are notoriously difficult to calibrate.

Optical Interferometry

Interferometry is a well-known technique that uses the wave nature of light to measure distances. De Groot gives an overview of its use in the measurement of surface topography.

In one typical arrangement, light emanating from a light source is split into two beams by a beam splitter. One of these two beams, the sample beam, is directed towards a surface of interest, and the other beam is directed towards a reference surface. Upon reflection at the surface of interest, the reflected sample beam travels back towards the beam splitter. The beam traveling towards the reference surface is reflected there and also travels back towards the beam splitter. The beam splitter then recombines these two beams and directs them to a detector configured to detect the intensity of incident light.

The intensity that is recorded by this detector is dependent on the phase relationship between the two beams after they have been recombined by the beam splitter. The phase relationship, in turn, is determined by the optical path length difference between the paths from the beam splitter to the respective surfaces. The optical path length of a beam is the product of the refractive index of the medium and the geometric distance the beam has traveled. If the optical path length difference is an integer multiple of the wavelength, the beams are said to interfere constructively and the detector will see an irradiance maximum. If the optical path difference however is an odd multiple of half the wavelength, the beams will interfere destructively and the detector will see an irradiance minimum. An analysis of this pattern of irradiance minima and maxima yields information about the relative optical path length difference between the sample beam and the reference beam.

Low-coherence Optical Interferometric Ranging

The phenomenon of interference between two beams is observable for a limited range of path length differences between the two beams. The characteristic attribute of a light source that describes this property is the coherence length, which is a measure of the path length over which the phase relationship of a beam remains stable. Hence, it characterizes the range of path-length differences over which interference can be observed. The coherence length of a light source is inversely proportional to its spectral bandwidth. For light sources with a high coherence length and narrow spectral bandwidth, such as some lasers, an interference pattern can be observed even for relatively large path-length differences, whereas for light sources with a broader emission spectrum the coherence length is substantially shortened, and interference can only be observed across a narrow range of path length differences. It is because of this presence of interference across a relatively narrow range of path-length differences that this type of broadband light sources with limited coherence length can be used to determine the distance to a reflective surface. Examples for such broadband light sources include light-emitting diodes, superluminescent diodes, incandescent bulbs, and arc lamps.

This is the principle of the well-known technique of low-coherence interferometric ranging. A low-coherence optical interferometric ranging system (LCOIRS) is a system that uses this approach to determine the distance to a reflective surface. A low-coherence Michelson interferometric ranging system (LCMIRS) relies on a Michelson interferometer to split, recombine and observe the optical path length difference between sample beam path and reference beam path. Low-coherence interferometric ranging is widely used in materials science and other disciplines to non-invasively determine the shape of reflective surfaces, such as the surfaces of optical elements or of semiconductor materials.

Sample Quantity vs Sample Properties.

There is potential for confusion in the context of optical technologies used to study liquids. Optical technologies are widely used to study the internal properties of liquids by passing optical beams through the interior of the liquid sample. The present invention is not concerned with the internal properties of the liquid sample, does not rely on light penetrating the sample, and is designed to be independent of the internal properties of the sample, which can remain unknown. We are concerned here exclusively with the use of optical-interferometric ranging to determine the position in space of the exterior, volume-defining, free surface of a liquid sample.

U.S. Pat. No. 5,323,229 by May discloses a device to measure the thickness of a transmissive sample. The sample attribute measured by the device described in U.S. Pat. No. 5,323,229 is the optical thickness, the product of the refractive index of the sample and the physical thickness of the sample. U.S. Pat. No. 5,323,229 describes a variety of means to obtain the physical thickness of the sample from the optical thickness, either by obtaining the refractive index of the sample in an independent measurement, or by placing the unknown sample into one arm of the interferometer and a standard of the same refractive index and defined thickness into the other arm of the interferometer. In the case of liquid samples such as films, U.S. Pat. No. 5,323,229 discloses a method of confining an additional aliquot of liquid in a cuvette of defined path length to this end. While this is of great utility in the assessment of the thickness of films of liquid produced in industrial quantities, the need to use additional liquid merely for the independent compensation of the sample's unknown refractive index makes this method inconvenient and impractical to use in the case of scarce and precious samples, as they are routinely encountered in life sciences laboratories.

U.S. Pat. No. 7,233,391 (B2) by Schermer describes a device and method to determine internal properties of a liquid sample confined in the wells of a microplate, such as the refractive index of the liquid, or molecular interactions between molecules immobilized on a container surface and analyte molecules in the liquid.

U.S. Pat. No. 6,958,816 (B1) by Dogariu discloses devices and methods to use dynamic light scattering to determine internal properties of liquids, in particular their rheological properties, such as their complex shear modulus, elasticity, viscosity, and viscoelasticity. While Dogariu's approach exploits optical interference between two beams, the sample beam results from reflections at particles suspended within the sample, rather than from a reflection at the sample surface, as in the present invention. The devices described in Dogariu determine the thermal motion of particles suspended in solution to deduce rheological properties rather than the position of the liquid surface to deduce the sample volume, the focus of the present invention.

U.S. Pat. No. 8,934,104 (B2) by Koerner illustrates the use of a device and method to apply optical interferometry to determine properties of biological or technical material over an unspecified sample volume. In the devices described by Koerner, an optical beam is reflected at the sample surface or within the sample to measure properties including the distance, depth, profile, form, undulation, roughness, optical thickness, and deviation from flatness. Koerner does not address the focus of the present invention, the sample volume.

SUMMARY

The present invention solves a ubiquitous problem in chemical and biological laboratories, the accurate, non-invasive determination of liquid sample volumes. For example, commonly used invasive methods, such as the photometric, ratiometric and fluorescent-dye methods destroy the utility of the sample for further use. In particular, such methods cannot be used to measure the change in the volume of the sample from one stage of investigation to the next. Acoustic methods lack the required resolution, both in the elevation of the sample surface and its variation in the horizontal plane across the container (the meniscus). Gravimetric methods require knowing the density of the liquid, and cannot be used if liquid is added to multiple, connected containers simultaneously, as in the common case of automated liquid handling equipment dispensing liquid into the wells of a microplate. Finally, most commonly used methods of sample-volume determination are forced to assume that the numerous wells of a microplate possess identical shapes and sizes.

The present invention exploits the great resolution, both vertical (nanometers) and horizontal (microns), of optical interferometry methods. Among such methods, those based on low-coherence light are especially attractive. The present invention exploits the established resolution of low-coherence interferometry to measure the volume of laboratory liquid samples accurately, non-invasively and quickly. Low-coherence interferometry is conveniently amenable to computerization and automation techniques, such as data analysis and the use of translation stages, the scanning of the sample beam of the interferometer and the pixelation of the interferometer beam.

The high resolution of low-coherence interferometry allows the topography of the surface of a liquid sample (the meniscus) to be accurately measured and factored into the determination of the sample volume, all executed by computer.

The invention also provides embodiment options, such as the use of optical fiber for the propagation of the optical beams of the interferometer. In such an embodiment, the path-length variation required by the low-coherence interferometer can be effected by piezo-electric stretching of a portion of the optical fiber.

OBJECTS OF THE INVENTION

Figure 1:
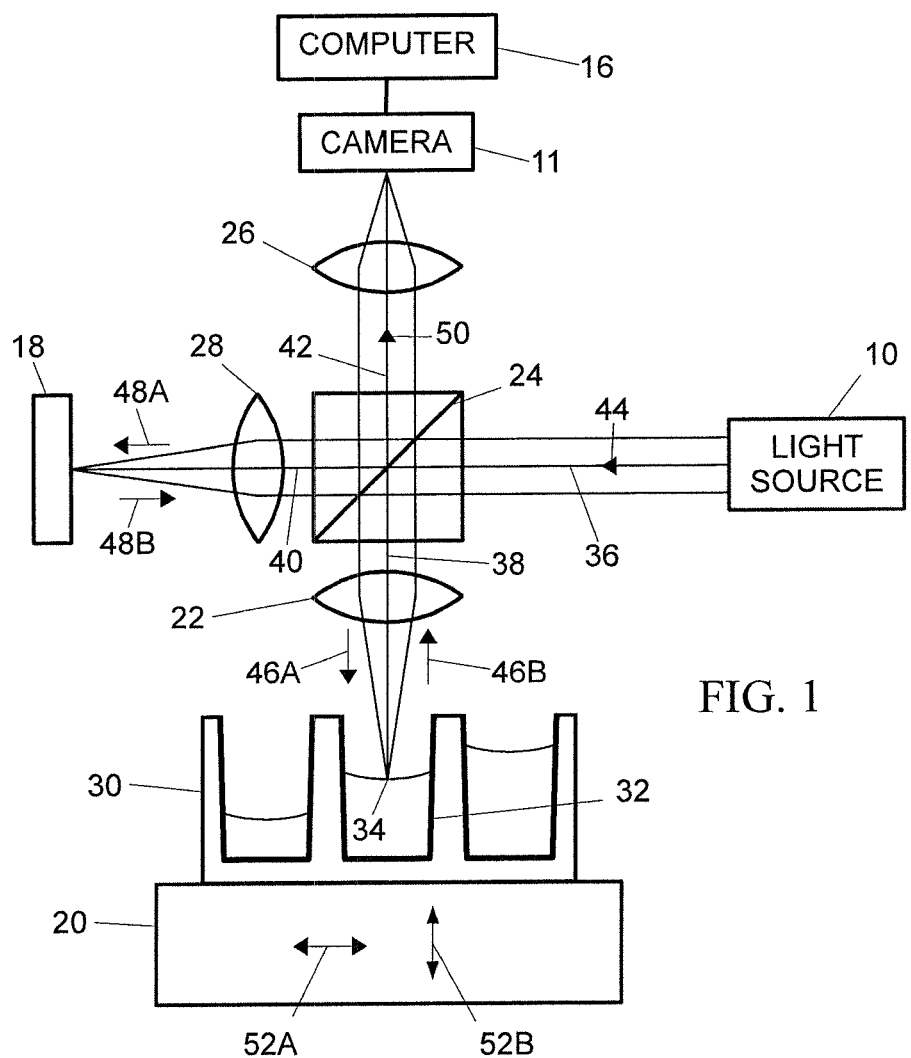
FIG. 1 Schematic drawing of a low-coherence optical interferometric ranging system positioned to measure the surface topography of spatially confined liquid samples.

One object of the invention is the measurement of liquid sample volumes that is accurate, non-invasive, fast, and amenable to automation.

Another object of the invention is the exploitation of both the lateral and axial resolution of low-coherence optical interferometric ranging to incorporate the shape of the liquid meniscus in the determination of liquid sample volumes.

Another object of the invention is a set of improvements in low-coherence optical interferometric ranging systems that provide greater convenience and efficiency.

DETAILED DESCRIPTION OF THE INVENTION

Reference Numerals
  10 light source
  11 camera
  12 detector
  13 amplifier
  14 analog-to-digital converter
  16 computer
  18 mirror
  20 XYZ translation stage
  22 lens
  24 beam splitter
  26 lens
  28 lens
  30 microplate
  32 microplate well
  34 liquid meniscus
  34' liquid meniscus
  36 beam exiting the light source
  38 portion of beam 36 reflected by beam splitter 24 towards microplate 30
  40 portion of beam 36 transmitted by beam splitter 24 towards mirror 18
  42 combined beam travelling to camera 11
  44 arrow indicating the direction of propagation of beam 36 exiting the light source
  46A arrow indicating the direction of propagation of beam 38 towards the sample
  46B arrow indicating the direction of propagation of beam 38 after reflection at liquid meniscus 34 towards beam splitter 24
  48A arrow indicating the direction of propagation of beam 40 towards mirror 18
  48B arrow indicating the direction of propagation of beam 40 towards beam splitter 24 afaer reflection at mirror 18
  50 arrow indicating the direction of propagation of combined beam 42
  52A arrows indicating a direction of horizontal movement of XYZ stage 20
  52B arrows indicating the direction of vertical movement of XYZ stage 20
  54 interferogram, intensity as a function of optical path length difference
  56 envelope of the interferogram
  58 maximum of the envelope of the interferogram
  60 fiber-optic circulator
  62 fiber-optic beam coupler
  64 optical delay adjuster
  66 fiber stretcher
  68 Faraday mirror
  70 delay compensator
  71 Faraday rotator
  72 probe head
  74 envelope detector
  76 optical fiber connecting light source 10 and circulator 60
  78 optical fiber connecting circulator 60 and fiber-optic beam coupler 62
  80 optical fiber connecting fiber-optic beam coupler 62 and delay adjuster 64
  82 optical fiber connecting delay adjuster 64 and fiber stretcher 66
  84 optical fiber connecting fiber stretcher 66 and Faraday mirror 68
  86 optical fiber connecting fiber-optic beam coupler 62 and delay compensator 70
  88 optical fiber connecting delay compensator 70 and Faraday rotator 71
  89 optical fiber connecting Faraday rotator 71 and probe head 72
  90 optical fiber connecting fiber-optic beam coupler 62 to detector 12
  92 arrow indicating direction of propagation of one beam in optical fiber 76

94 arrow indicating direction of propagation of one beam in optical fiber 78

96 arrow indicating direction of propagation of one beam in optical fiber 80

98 arrow indicating direction of propagation of one beam in optical fiber 82

100 arrow indicating direction of propagation of one beam in optical fiber 84

102 arrow indicating direction of propagation of one beam in optical fiber 84

104 arrow indicating direction of propagation of one beam in optical fiber 82

106 arrow indicating direction of propagation of one beam in optical fiber 80

108 arrow indicating direction of propagation of one beam in optical fiber 86

110 arrow indicating direction of propagation of one beam in optical fiber 88

111 arrow indicating direction of propagation of one beam in optical fiber 89

112A arrow indicating direction of propagation of beam propagating towards the sample 112B arrow indicating direction of propagation of beam reflected by the sample 113 arrow indicating direction of propagation of one beam in optical fiber 89

114 arrow indicating direction of propagation of one beam in optical fiber 88

116 arrow indicating direction of propagation of one beam in optical fiber 86

118 arrow indicating direction of propagation of one beam in optical fiber 90

120A arrow indicating direction of propagation of beam propagating towards the sample from underneath 120B arrow indicating direction of propagation of beam reflected by the sample Description of First Embodiment In this embodiment, depicted in FIG. 1, a low-coherence optical interferometric ranging system, more specifically a low-coherence Michelson interferometric ranging system, is positioned above a microplate 30 in such a manner that the elevation of the surface of microplate 30 or the surface 34 of a volume of liquid contained in the wells 32 of microplate 30 (shown here) can be measured. Camera 11 and imaging lenses 22 and 26 are positioned above a well 32 of a microplate 30 containing a volume of liquid with a meniscus 34 in such a way that a focused image of the liquid surface is formed on camera 11. Examples for a suitable camera include a video camera, which contains a rectangular array of detector elements, or a line scan camera, which contains a single line of detector elements. In an alternative embodiment, a single element detector with an analog-to-digital converter could replace camera 11. A beam splitter 24 is positioned between camera 11 and microplate 30, more specifically, it is positioned between imaging lenses 22 and 26. Light source 10 illuminates beam splitter 24 in such a way that light emanating from the light source, indicated by beam 36, is split into two beams. The first of these two beams, the sample beam 38, is directed towards microplate 30, here towards liquid surface 34, in the direction indicated by arrow 46A. The other beam, reference beam 40, is directed towards reference mirror 18. Upon reflection at the liquid surface 34, the reflected portion of sample beam 38 travels back towards the beam splitter 24 in the direction indicated by arrow 46B. A portion of this reflected sample beam traveling in the direction indicated by arrow 46B is transmitted by beam splitter 24 as a part of the combined beam 42, travels in the direction indicated by arrow 50, and impinges upon camera 11. A portion of reference beam 40 traveling in the direction indicated by arrow 48A is reflected by reference mirror 18 and travels back towards beam splitter 24 in the direction indicated by arrow 48B. Upon reflection by beam splitter 24, a portion of this reflected reference beam traveling in the direction indicated by arrow 48B forms a part of the combined beam 42, traveling in the direction indicated by arrow 50 towards camera 11.

Reference mirror 18 is mounted in such a way that lenses 28 and 26 form a focused image of the surface of reference mirror 18 on camera 11 that is superimposed on the focused image of the liquid surface 34 that is formed on camera 11 by lenses 22 and 26. In one embodiment, reference mirror 18 is chosen such that its reflectivity is comparable to the reflectivity of a typical liquid surface 34 or of a typical plastic material used in microplates 30, thus ensuring that the intensities of the reflected reference and sample beams are comparable. An uncoated glass window is an example of a suitable reference mirror. Reference mirror 18 is further mounted in such a way that an interference maximum 58 of the envelope 56 of interferogram 54 is observed on camera 11 while both images of reference mirror 18 and liquid surface 34 are in focus on camera 11. This latter condition implies that reference mirror 18 is adjusted in such a way that the optical path lengths traversed by beam 38 and by beam 40 are equal. Microplate 30 is mounted on XYZ stage 20 in such a way that it may be translated in the direction indicated by arrows 52B. A provision is made to read and record the current position of the microplate 30 relative to beam splitter 24. For example, XYZ translation stage 20 can be a manual or computer-controlled translation stage, the current position of which can read or recorded.

Microplate 30 is further mounted in such a way that XYZ translation stage 20 may translate it in the horizontal plane indicated by arrows 52A to facilitate ranging the distance to different areas of microplate 30, such as the liquid meniscus 34 in different wells 32 of microplate 30 or the top rim of a well 32 or the bottom of a well 32 which does not contain liquid. Provisions are made so that the lateral position of microplate 30 relative to the low-coherence optical interferometric ranging system can be read and recorded.

Operation of First Embodiment

Camera 11 acquires a sequence of images. Between images, the optical path length difference between the sample and reference arms of the low-coherence optical interferometric ranging system is incremented. To that end, the difference between the optical path length of beam 40 and the optical path length of beam 38 is altered by vertically translating microplate 30 in the direction indicated by arrows 52B using translation stage 20. In an alternative embodiment, the reference mirror 18 could be translated relative to the beam splitter along the optical axis of beam 40 instead. If microplate 30 is translated relative to the detector, care is taken to ensure that the sample remains sufficiently in focus. For the short coherence lengths on the order of 10-20 μm of typical broadband light sources 10 suggested here, the maximum scan range that is needed to record an interferogram is much smaller than the working distance of the imaging lens (typically 25-50 mm), so the sample does not appreciably move out of focus. For each image, the current optical path length difference is recorded. It is obtained from the current relative position of the reference mirror 18 or of the microplate 30 or both, if both are translated. Alternatively, camera 11 is operated in video mode at a fixed, constant frame rate and microplate 30 or reference mirror 18 are translated at constant speed. In this manner, a constant increment in optical path length difference between subsequent frames of the video is ensured. In this method, the exposure time of the camera has to be kept sufficiently short and the speed of the translation stage sufficiently low so as to avoid motion blur.

Data Processing

In a subsequent step, the recorded intensity value for a set of pixels is extracted from each image acquired by camera 11. Each image has been selected such that it corresponds to one optical path length difference between sample and reference beams. A selection of pixels is chosen for this analysis in such a way that points of interest across the liquid surface 34 or across other areas on the surface of microplate 30 are imaged onto these selected pixels of camera 11. For example, a line that transects the center of a cylindrically symmetric well 32 is a suitable selection. In this case, one would select a set of pixels of camera 11 onto which this line is imaged.

Selecting more pixels of camera 11 results in a better lateral resolution across the surface 34 of the liquid in well 32. However, analyzing data from more pixels requires more time. This limits the number of elevation scans that can be acquired per unit time. Therefore, the time it takes to acquire an elevation scan for each well 32 of interest in a microplate 30 increases and the total number of microplates 30 that can be scanned in a given time decreases.

For each of the selected pixels of camera 11, the value of the pixel intensity is plotted as a function of the optical path length difference between reference beam and sample beam. This results in a graph called an interferogram for each pixel of camera 11. An illustrative example of such a graph is depicted as 54 in FIG. 2. The interferogram 54 consists of a sinusoidal function with changing amplitude. The frequency of the sinusoidal fluctuations of 54 is determined by the ratio of optical path length difference between data points and the wavelength of the light source, whereas the slower fluctuation of the envelope 56 of interferogram 54 is determined by the coherence length of the light source 10.

Figure 2:
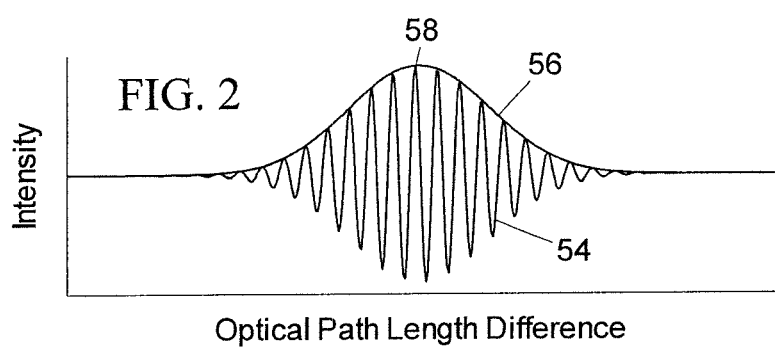
FIG. 2 Typical interferogram produced by a low-coherence optical interferometric ranging system, depicting the constructive interference of the sample and reference optical beams with the variation of the optical path length of either the sample or reference beam.

Subsequently, a mathematical algorithm is applied to interferogram 54 to obtain its envelope 56 depicted in FIG. 2. The Hilbert transform, for example, is one suitable algorithm. In a subsequent step, the maximum 58 of the envelope 56, which corresponds to its center, is identified. Using a Levenberg-Marquardt algorithm to fit a Gaussian function to the data for the envelope 56 is an example of a suitable method to accomplish this. The maximum 58 of the envelope 56 determined in this manner corresponds to the location of the surface 34 depicted in FIG. 1 as a function of relative path length difference between sample and reference beams for the area on the liquid surface 34 that is imaged onto this pixel of camera 11.

Distance Calibration

The setup in this embodiment of the invention is calibrated in such a way that a given path length difference is unambiguously related to the location of the surface of microplate 30 from which the reflection is observed. In one possible way to accomplish this calibration, a plane glass plate is placed into a defined position in the sample beam path. An uncoated glass plate with parallel surfaces and known thickness is a suitable test sample, as the proportion of incident light reflected at its surface is comparable to that reflected at the surface of typical liquids. One suitable method for positioning the glass plate is to remove microplate 30 from the flat surface of XYZ translation stage 20 on which it rests during operation and replace it with the glass plate. One then varies the optical path length difference between sample and reference beam by actuating XYZ translation stage 20 in the vertical direction indicated by arrows 52B until one observes a maximum 58 of envelope 56 of interferogram 54 at a chosen pixel of camera 11 resulting from the reflection of the sample beam 38 at the top surface of the glass plate. One then records the position of XYZ translation stage 20. Subsequently, the glass plate is removed and replaced with microplate 30.

Then, an interferogram 54 is recorded for one or several points on the surface of microplate 30 as discussed above. If the maximum 58 of the envelope 56 occurs for the same position of XYZ translation stage 20 as previously recorded, the elevation of microplate 30 at this position is identical to the thickness of the glass plate used for calibration. If the maximum 58 of envelope 56 occurs at a different vertical position of XYZ translation stage 20, the elevation of microplate 30 is easily derived from the displacement of XYZ translation stage 20 from its previously determined reference position and the known thickness of the glass plate.

This discussion assumes that the reflection giving rise to interference occurs at the topmost surface of the microplate 30. For reflections at internal interfaces in the microplate, such as the interface between the liquid in well 32 and the bottom of well 32, the refractive index along the sample beam path has to be taken into account to correctly derive the elevation of the internal interface above the reference position.

In this manner, the setup is used to perform an individual elevation measurement with each pixel of camera 11. Depending on the lateral position of microplate 30 relative to camera 11, the setup can measure the elevation of liquid surfaces 34 in the wells 32 of a microplate 30 or of plastic features on the surface of the microplate, such as the vertical position of the bottom of an empty well 32 or the vertical position of a ridge between wells 32. Together with a knowledge of the depth of well 32, which is to be measured independently, this allows the user to calculate the liquid fill height in well 32, i.e. the elevation of the liquid surface 34 above the bottom of well 32.

Calculation of Liquid Volume

Wells 32 in microplates 30 come in a variety of shapes, with square, round, or diamond-shaped cross sections, among others. Because microplates 30 are produced by molding, the walls of their wells 32 are not at right angles to the plane of the microplate 30. Rather, the wells 32 are larger at the top than at the bottom because of the draft angle of the mold. An axisymmetric well 32 with a round cross section and a flat bottom, therefore, constitutes a section of a cone rather than a cylinder. Similarly, a well with a rectangular cross section and a flat bottom constitutes a section of a pyramid.

The volume of liquid in a well 32 with a flat bottom and a round cross section, a bottom radius r, and a wall angle $\gamma$ that is filled to the liquid fill height h is calculated as follows. This formula assumes that the liquid forms a horizontal, planar meniscus.

$$V = \pi \cdot r^2 + \pi \cdot r \cdot \tan\gamma \cdot h^2 + \frac{1}{3} \cdot \pi \cdot (\tan\gamma)^2 \cdot h^3$$

A mathematical analysis shows that of the three quantities in this equation, the well volume V is most sensitive to the radius r at the bottom of the well. Specifically, the values for the partial derivatives of the volume with respect to the three parameters bottom radius r, tangent of the draft angle tan γ, and fill height h are computed for typical well and fill height dimensions. These values correspond to a sensitivity of the uncertainty in well volume with respect to the uncertainty in one of the parameters. Typical manufacturer tolerances for the well bottom radius in 96-well microplates are on the order of 1%. The analysis described above shows that for typical well dimensions in a 96-well plate such a 1% uncertainty in the bottom radius of a well leads to an uncertainty for the well volume of up to 5%, depending on the fill volume of the well. This consideration shows that relying on manufacturer tolerances, the best accuracy that could be achieved would be 5%. To improve this, microplates have to be measured accurately before use for volume verification applications such as the one presented here. U.S. Pat. No. 7,187,455 B2 explicitly claims an independent verification of well dimensions as an aspect of the method described therein.

In-Situ Measurement of Well Dimensions

In light of the need discussed above, an aspect of this invention makes provisions to measure important dimensions of the well 32 on the same instrument. In one suitable arrangement, the instrument provides for a digital camera with a telecentric imaging lens that is mounted such that the optical axis is perpendicular to the plane of the microplate. The camera acquires an image of each well that shows the entire rim of the top or the bottom of the well. The magnification of this portion of the optical system comprising this camera and imaging lens is determined separately. An attached computer allows for automated processing of these images to measure the dimensions of the top or the bottom of the well 32.

These measured dimensions are then used to more accurately calculate the volume of well 32. Because the elevation-scanning aspect of the system is used to furnish measurements of the elevation of the well top, errors in imaging scale due to a shift of the object along the optical axis are controlled.

Meniscus Shape

If the selected pixels of camera 11 lie on a straight line, and microplate 30 is positioned such that liquid surface 34 in a well 32 is imaged onto these pixels of camera 11, the resulting plot of the lateral pixel location vs. the optical path length difference corresponding to maximum 58 of envelope 56 of interferogram 54 yields a representation of a lateral cross section of meniscus 34.

Figure 3A:
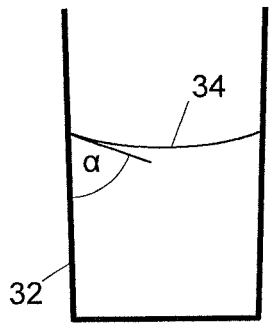
FIGS. 3A, 3B, 3C, 3D, and 3E illustrate typical meniscus shapes of a liquid sample confined in a microplate well.
Figure 3B:
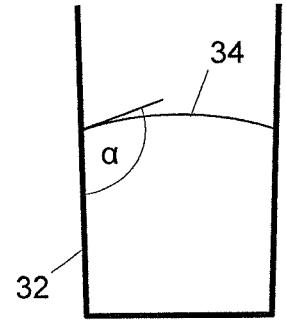
Figure 3C:
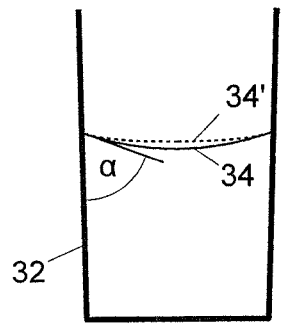

In most cases of experimental relevance, meniscus 34 is curved rather than planar. The utility of a device that measures liquid volumes in microplates is, therefore, greatly increased if it can accommodate liquids that give rise to curved menisci. A curved meniscus is either convex or concave, depending on the liquid in well 32 and the material of microplate 30, specifically the material of the walls of well 32. FIG. 3A-C illustrates this schematically.

FIG. 3A depicts a cross section through a well 32 that contains a liquid with a surface 34 that gives rise to a concave meniscus. The contact angle α between liquid surface 34 and the wall of well 32 is less than 90° in this case.

FIG. 3B depicts another such cross section. Liquid surface 34 gives rise to a convex meniscus and the contact angle α between liquid surface 34 and the wall of well 32 is larger than 90°.

FIG. 3C illustrates two cross-section through two wells 32 containing two liquids with different capillary length, giving rise to a surface 34 and a surface 34', respectively. The capillary length of a liquid is a characteristic measure of how quickly the angle between the liquid surface and the horizontal decreases with increasing distance from a wall that the liquid touches.

For clarity of this illustration, it is assumed in FIG. 3C that the volumes of liquid are adjusted such that the contact point between the cross-section of the wall of well 32 and the cross section of the liquid surface coincide, i.e. the liquid fill heights at the point where surfaces 34 and 34' of the liquids touch the wall of well 32 are identical. The contact angle α between surface 34 of the first liquid and the wall of well 32 and the contact angle between surface 34' of the second liquid and the wall of well 32 are also assumed to be identical. The capillary length is different between the two liquid volumes with surfaces 34 and 34'.

If meniscus 34 is curved, measuring liquid fill height at one point in well 32 is not sufficient for an accurate calculation of liquid volume.

Figure 3D:
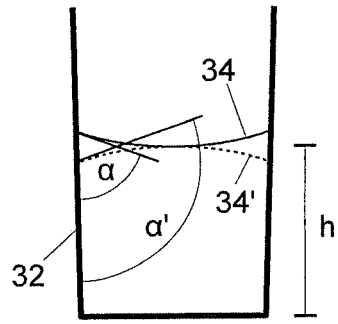

To illustrate this, FIG. 3D depicts an example of two superimposed cross-sections of a well 32 that contains two liquids with surfaces 34 and 34'. The fill height h at the center of well 32 is identical for both liquids, but the contact angle α between the wall of well 32 and the liquid with surface 34 is smaller than the contact angle α' between the wall of well 32 and the liquid with surface 34'.

In FIG. 3D, a difference between the volume of liquid giving rise to surface 34 and the volume of liquid giving rise to surface 34' is readily apparent.

Figure 3E:
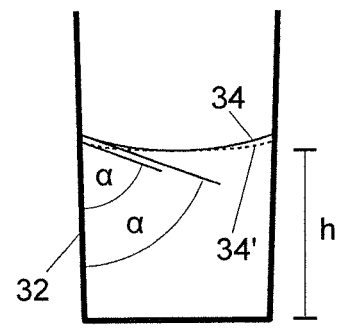

FIG. 3E illustrates this effect for two liquids with different capillary length. For this illustration, the volumes of liquid have been chosen such that the fill height h at the center of well 32 as well as the contact angle α between the liquid surfaces 34 and 34' and the wall of well 32 are identical. In FIG. 3E, the liquids that give rise to surfaces 32 and 32' differ in their capillary length. As in FIG. 3D, a difference between the volume of liquid giving rise to surface 34 and the volume of liquid giving rise to surface 34' is readily apparent in FIG. 3E also.

The examples in FIGS. 3D and 3E illustrate how the different shape of surfaces 34 and 34' leads to differences in the volume of liquid, even if the liquid fill height h in the center of well 32 is the same. In this embodiment, the actual shape of the liquid meniscus is, therefore, measured by measuring the fill height h at several points on the surface of the liquid contained in the well. It is then accounted for in the calculation of the liquid volume.

Extrapolation of Meniscus Shape

Experimentally, for liquid filled wells with a curved meniscus, a decrease in contrast between successive interference minima and maxima is observed as radial distance from the center of well 32 increases. Examples of physical effects contributing to this phenomenon are the increased slope of liquid surface 34 further away from the center, and the limited numerical aperture of the imaging lens 22. In some cases, elevation measurements as described in this document may only be obtained from areas near the center of well 32. In such a case, obtaining a representation of the cross section of meniscus 34 across the entirety of well 32 is achieved by extrapolation. In these cases, the shape of meniscus 34 is extrapolated from the area where it can be measured to the edge of well 32, where liquid surface 34 meets the wall of well 32. To do this, an aspect of this invention takes advantage of the known equations that govern the shape of the free surface of any liquid. The Laplace-Young equation is an example of one such equation. Specifically, one may apply the following algorithm.

Select a region of interest in the collected images that make up the interferogram such as a line that transects the center of well 32, and obtain the elevation of the liquid surface 34 along this line in the manner described above. This elevation profile corresponds to the experimentally measured meniscus shape.

Guess a value for the capillary length and the contact angle.

Perform a numerical integration of the Laplace-Young equation for this pair of guesses. One possible algorithm to perform this numerical integration is the "shooting method" as described in Pozrikidis and in Press et al. This integration yields the elevation of the liquid meniscus relative to the apex for the guessed capillary length and contact angle.

Quantify how closely the shape of the meniscus that results from the calculation above matches the shape of the experimentally measured meniscus by computing a goodness-of-fit measure such as the sum of squared residuals.

Modify the guesses for capillary length and contact angle in such a way that goodness of fit increases for the region for which measurements exist and repeat the steps above until the goodness-of-fit is sufficient. The guesses are modified following well-known numerical algorithms for minimizing a function of two variables, such as those found in Press et al. Record capillary length and contact angle for the numerical solution of the surface shape.

Together with the fill height at the center of the well, and the known shape of the well walls, this information is sufficient to compute the volume of liquid contained in the well.

Description of Second Embodiment

Figure 4:
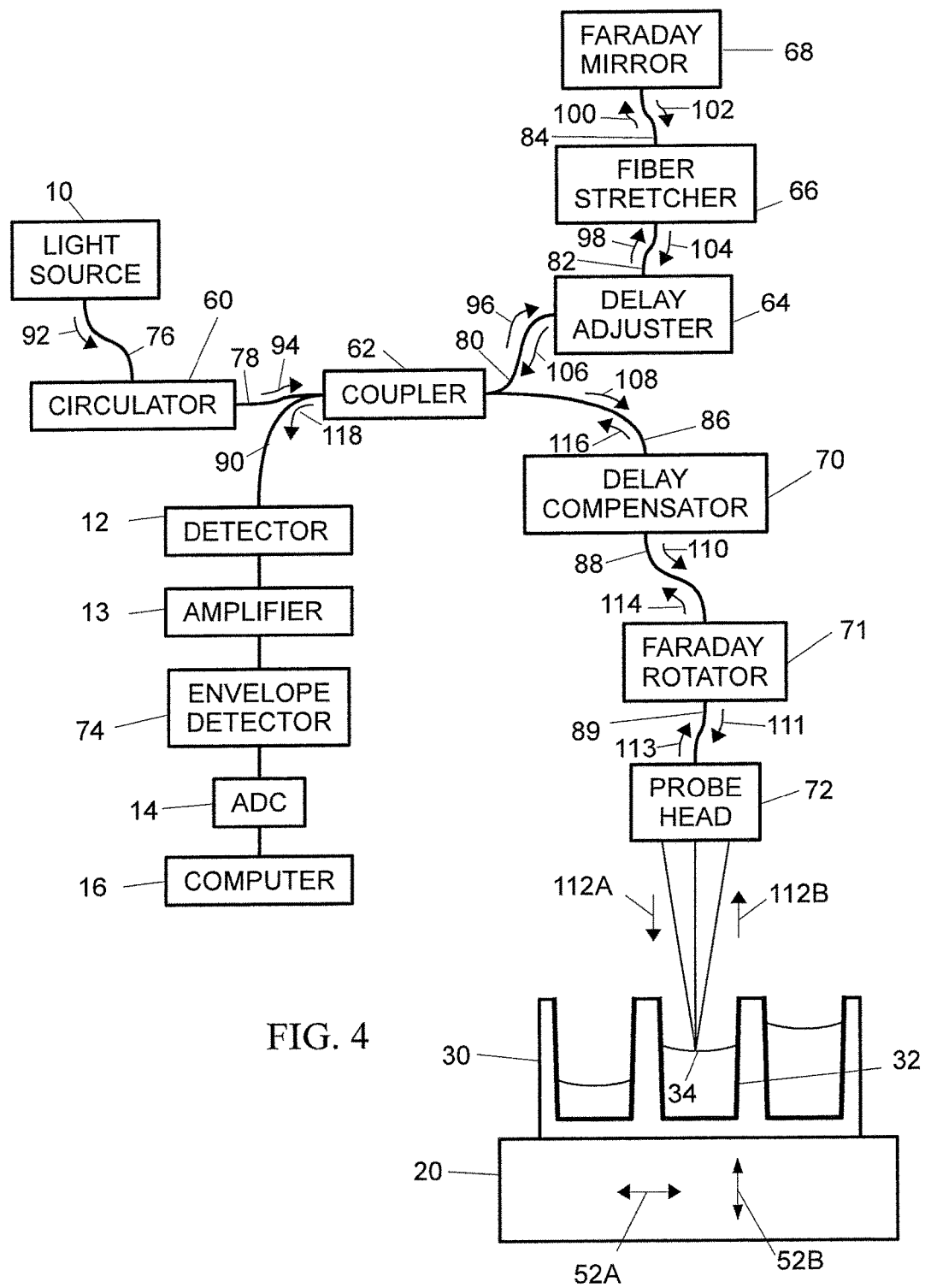
FIG. 4 Configuration of components of a low-coherence optical interferometric ranging system in which the interferometer beams propagate in optical fibers.

This embodiment relies on a fiber-optic low-coherence Michelson interferometric ranging system known in prior art. Its functional elements are depicted in FIG. 4.

Fiber-based optical interferometers, such as fiber-optic low-coherence optical interferometric ranging systems rely on single-mode optical fibers. This embodiment, therefore, uses a light source that can be coupled efficiently into a single-mode optical fiber while at the same time offering the benefit of a relatively short coherence length. A superluminescent diode is such an optical source and is commonly used in fiber-optic low-coherence optical interferometric ranging systems. A superluminescent diode with a center wavelength of 1310 nm such as model # EXS210032-02 manufactured by Exalos AG of Schlieren, Switzerland is a suitable diode.

Light from light source 10 travels in the direction indicated by arrow 92 through optical fiber 76 and enters optical circulator 60. Light exits optical circulator 60, travels through optical fiber 78 in the direction indicated by arrow 94, and enters fiber-optic coupler 62.

Reference Beam

A portion of the light that entered fiber-optic coupler 62 through optical fiber 78 in the direction indicated by arrow 94 exits fiber-optic coupler 62 through optical fiber 80 in the direction indicated by arrow 96 and enters delay adjuster 64. Delay adjuster 64 matches the optical path lengths traversed by the reference and sample beams of the interferometer in such a way that interference can be observed on detector 12. Light exits delay adjuster 64 through optical fiber 82 in the direction indicated by arrow 98 and enters fiber stretcher 66. The high-efficiency fiber stretcher model PZ2 manufactured by Optiphase/Halliburton of Van Nuys, Calif. is a suitable fiber stretcher. A high voltage amplifier circuit is provided to drive the piezo-electric fiber stretcher with a periodic signal of sufficient amplitude to cause it to induce the desired optical path length difference between sample and reference beams by stretching the fiber. Light exits fiber stretcher 66 through optical fiber 84, travels in the direction indicated by arrow 100, and enters Faraday mirror 68. Faraday mirror 68 reflects incident light and rotates its plane of polarization by 90° and is used here to limit the loss of interference contrast due to stress-induced birefringence in the optical fiber wrapped around the mandrel of piezo-electric fiber stretcher 66. Faraday mirror 68 reflects a portion of the light back into fiber 84, where it travels in the direction indicated by arrow 102 and re-enters fiber stretcher 66. Light exits fiber stretcher 66 through optical fiber 82 in the direction indicated by arrow 104 and enters delay adjuster 64. Light exits delay adjuster 64, travels through optical fiber 80 in the direction indicated by arrow 106, and re-enters fiber-optic coupler 62. The optical path described above, from coupler 62 to Faraday mirror 68 and back to coupler 62 makes up the reference beam of the low-coherence Michelson interferometric ranging system.

Sample Beam

Another portion of the light that entered fiber coupler 62 through fiber 78 in the direction indicated by arrow 94 exits fiber coupler 62 through optical fiber 86 in the direction indicated by arrow 108 and enters delay compensator 70. Delay compensator 70 ensures that the optical path length traversed by the sample beam of the low-coherence interferometric ranging system is similar to within the coherence length of light source 10 to the optical path length traversed by the reference beam, if fiber stretcher 66 in the reference beam is not actuated. A second piezo-electric fiber stretcher that is manufactured to have a path length that is closely matched to the piezo-electric fiber stretcher 66 in the reference beam and otherwise identical is one possible choice for a delay compensator 70. In this case, the effective scan range of the instrument can be doubled by driving this second fiber stretcher in the sample arm with a signal of opposite polarity to the signal driving fiber stretcher 66 in the reference arm. Light exits delay compensator 70 through optical fiber 88 in the direction indicated by arrow 110 and enters Faraday rotator 71. Faraday rotator 71 rotates the plane of polarization by 45°. Light transmitted twice through Faraday rotator 71, once before and once after having been reflected at the sample, therefore, has a plane of polarization that is rotated 90° to the incident light, and the Faraday rotator thus plays the same role as Faraday mirror 68 in the reference arm. It is used here to limit the loss of interference contrast due to stress-induced birefringence in the optical fiber wrapped around the mandrel of delay compensator 70. Light exits Faraday rotator 71 through optical fiber 89 in the direction indicated by arrow 111 and enters probe head 72. Probe head 72 images the end face of fiber 89 onto an area on the surface of microplate 30, giving rise to a beam traveling in the direction indicated by arrow 112A, which travels from probe head 72 towards microplate 30. Microplate 30 contains a multiplicity of wells 32. Wells 32 contain a liquid that forms a meniscus 34, which reflects a portion of the beam propagating in the direction indicated by arrow 112A. Probe head 72 images reflected light traveling in the direction indicated by arrow 112B back into optical fiber 89, where it travels in the direction indicated by arrow 113 and enters Faraday rotator 71. Light exits Faraday rotator 71 through optical fiber 88, where it travels in the direction indicated by arrow 114 and enters delay compensator 70. Light exits delay compensator 70 through optical fiber 86 in the direction indicated by arrow 116 and re-enters fiber-optic beam coupler 62. The optical path described above, from coupler 62 to a liquid surface 34 or another feature on the surface of microplate 30 and back to coupler 62 makes up the sample beam of the low-coherence Michelson interferometric ranging system.

Detection

Light exits beam coupler 62 through fiber 90 in the direction indicated by arrow 118 to impinge upon detector 12. A high speed InGaAs PIN photodiode such as model FD80 manufactured by Fermionics Opto-Technology of Simi Valley, Calif. is an example of a suitable detector. Amplifier 13 contains a transimpedance amplifier to convert the electrical current signal from photodetector 12 to a voltage signal. Amplifier 13 also contains a DC-coupled and an AC-coupled subsequent stage. The DC-coupled stage leads to an output that provides a voltage signal that is proportional to the proportion of light reflected by the sample surface and collected by the sample arm of the interferometer and thus allows for monitoring the focusing of probe head 72. The AC-coupled stage removes the DC background of the signal, further amplifies this voltage signal and feeds it to envelope detector 74. Envelope detector 74 is an asynchronous demodulator. Its purpose is to extract the envelope 56 from a signal 54 (see FIG. 2) at its input. A circuit based on the integrated circuit AD 834 provided by Analog Devices of Norwood, Mass. and substantially similar to that shown in FIG. 18 of the datasheet for the integrated circuit AD 834 provided by Analog Devices is an example of a suitable circuit. The electrical output signal of envelope detection circuit 74 is fed into an analog-to-digital converter (ADC) module 14. The output of analog-to-digital converter module 14 is fed into a computer 16 for storage and further manipulation.

Operation Second Embodiment

Light Source and Optical Path Length Modulation

Light source 10 is operated in such a manner that it emits light of an intensity that remains substantially constant with time. A periodic electrical signal is applied to piezo-electric fiber stretcher 66, which causes it to periodically change the length of the optical path the light in the reference beam traverses. As an example, a triangular waveform may be applied. The frequency of the triangular waveform depends on the needs of the experiment and the characteristics of piezo-electric fiber stretcher 66. In particular, it determines an upper limit on how many elevation scans the instrument can perform in a given period of time. A frequency of between 200 and 2000 Hz is one suitable frequency range for the fiber stretchers used here. As an example, to measure the liquid fill height in a typical well 32 in a microplate 30, the following steps are taken. In order to measure the elevation of a point on the sample surface using the fiber-optic low-coherence optical interferometric ranging system described here, an interference maximum 58 needs to be observed which occurs when reference and sample beam paths of the interferometer are equal.

Further, the output face of fiber 89 and the optics in probe head 72 form a confocal imaging system. Therefore, light reflected by the sample can only re-enter fiber 89 efficiently if the distance between probe head 72 and sample surface 34 is such that the optics in probe head 72 form a focused image of the fiber end face on the sample surface and the inclination of the sample surface is such that reflected light falls within the sample-side numerical aperture of probe head 72.

In this embodiment, delay adjuster 64 is adjusted such that the optical path lengths of the sample and reference arms of the interferometer are substantially equal while fiber stretcher 66 is at rest.

Then, XYZ translation stage 20 is translated vertically in the direction indicated by arrows 52B until reflected light from the sample is observed on detector 12 as indicated by a voltage signal on the DC-coupled output stage of amplifier 13, indicating that the sample surface is within the confocal region of the probe head. The vertical position of XYZ translation stage 20 is then recorded.

Then, fiber stretcher 66 is driven with a triangular waveform, causing the optical path length of the reference arm of the interferometer to vary in a substantially triangular waveform as well.

At the output of the AC-coupled output stage of amplifier 13, an interferogram substantially similar to interferogram 54 is now observed. Envelope detector 74 provides the envelope of that signal, which is sampled by analog-to-digital converter 14 and stored in computer 16, which is used to determine the maximum 58 of the envelope.

To obtain the elevation of the sample surface from this measurement, the vertical position of XYZ stage 20 and the current optical path length of fiber stretcher 66 is needed.

To record the current optical path length of fiber stretcher 66, and thus the current length of the reference arm of the interferometer at each sample recorded by analog-to-digital converter 74, a method known in the art is used. One such method of determining the path length of a fiber-optic low-coherence interferometer by using a coherent light source together with a low-coherence light source is described for an optical autocorrelator in U.S. Pat. No. 6,847,453 B2. In one possible embodiment, a coherent light source at a wavelength different from that of light source 10 is coupled into the interferometer together with light source 10. Light from this coherent light source passes through the reference arm of the interferometer in the same manner as light from light source 10. In the sample arm, the dominant reflected beam for the coherent light source is generated by a reflection at the sample-side end face of fiber 89. While all other fiber end-faces in the low-coherence interferometric ranging system discussed here are chosen with an industry standard angled polish to avoid spurious back-reflections from these interfaces within the beam path, the sample side end face of fiber 89 is chosen with a perpendicular polish. Light from light source 10 will also be reflected at this perpendicular output face, but it will not contribute to an interference signal, because the distance of the sample-side end face of fiber 89 from the sample surface is much greater than the coherence length of light source 10. The length of the portion of the sample beam path from coupler 62 to the sample-side end face of fiber 89 remains constant during operation of this device. Thus, the interference signal from the coherent light source can be used to determine the path length of the reference beam, and thus the current length of fiber stretcher 66 for each sample recorded by analog-to-digital converter 74.

Signal Acquisition

A measurement of the liquid fill height in a well 32 of a microplate 30 proceeds in the following manner. Microplate 30 is translated horizontally using XYZ translation stage 20 such that a point of interest on the surface of microplate 30 is positioned in the area that is being interrogated by probe head 72. In the case of measuring the elevation of the liquid surface 34 in a well 32, the area to be interrogated should be on a line that transects the center of the well.

Next, XYZ stage 20 is moved vertically such that liquid surface 34 is in the confocal region of probe head 72, and the vertical position of XYZ stage 20 is recorded. Next, fiber stretcher 66 is actuated, and the fiber stretcher length corresponding to the maximum 58 of the envelope 56 of an interferogram 54 is recorded. The vertical position of XYZ stage 20 and the current length of fiber stretcher 66 together uniquely define the elevation of the sample surface 34 giving rise to the reflection being observed.

A calibration of the elevation measurement using a plane glass plate can be performed analogously to the method described for the first embodiment above.

To measure the elevation of liquid surface 34 at several points, XYZ translation stage 20 is translated in the horizontal plane in the direction indicated by arrows 52A in between elevation measurements. In an alternative embodiment, a scanning mirror is used to direct the sample beam to different points on liquid surface 34. If the elevation of the liquid surface is determined on several points along a line that transects the center of the well, the shape of the meniscus can be measured and included in the calculation of the sample volume as described for the first embodiment above.

Other Embodiments

Detecting Phase Separation of Immiscible Liquids

Figure 5:
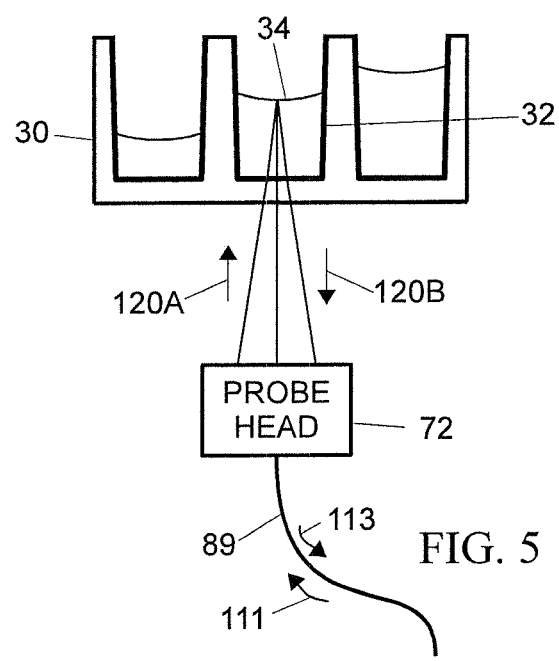
FIG. 5 Schematic diagram showing interferometric ranging of a liquid-sample surface from below.

Any surface or interface between two media with different indices of refraction gives rise to a reflection, and its position can therefore be measured with a low-coherence optical interferometric ranging system. Another embodiment of this invention is, therefore, used to detect whether two or more immiscible liquids have separated into two or more phases in well 32 as depicted in FIG. 4 or 5. A well 32 that contains two liquids which have separated into two phases gives rise to an additional reflection. This reflection is in addition to and at an elevation between the reflection at bottom of well 32 and surface 34 of the liquid, i.e. the liquid-air interface.

Measuring Liquid Volumes in a Microplate with a Lid

Yet another embodiment of this invention is used to determine the liquid fill height in a microplate 30 that is covered by a transparent lid. In FIG. 4, the sample beam passes through this lid (not shown) in the direction indicated by arrow 112A before being reflected at surface 34 of the liquid in well 32 or another region of interest on the surface of microplate 30. The reflected beam, traveling in the direction indicated by arrow 112B, passes back through this lid before being imaged into optical fiber 89 by probe head 72.

Direct Measurement of Liquid Fill Height

According to another aspect of the invention, the liquid fill height in well 32, i.e. the elevation of liquid surface 34 above the bottom of well 32, is obtained directly from the optical path length difference between the reflection from surface 34 of the liquid and the reflection from the interface between the liquid and the bottom of well 32. The optical path length difference between these two surfaces is the product of the refractive index of the liquid in the well and the actual liquid fill height. To obtain the liquid fill height, the refractive index of the liquid has to be known or it has to be determined independently.

One suitable method to determine the refractive index of the liquid is the following: the sample liquid is contained in a container with two parallel walls which are arranged perpendicular to the optical axis and with a known distance between each other. The container is filled with the sample liquid and a measurement of the optical path length difference between the two interfaces between container and liquid is performed in the manner of an elevation scan described above. From this, the refractive index is calculated by dividing the optical path length (which is measured by the interferometer) by the known distance between the walls of the container. To arrive at the liquid fill height, the measured optical path length difference between surface 34 of the liquid in well 32 and the bottom of well 32 is divided by the refractive index determined in this manner.

Direct Measurement of Liquid Fill Height through the Bottom of the Plate

According to yet another embodiment of this invention, a direct measurement of liquid fill height can be carried out by sensing the elevation of liquid surface 34 through the bottom of microplate 30, as depicted in FIG. 5. In this embodiment, the elevation of the liquid surface 34 above the bottom of well 32, is also obtained directly from the optical path length difference between the reflection from surface 34 of the liquid and the reflection from the interface between the liquid and the bottom of well 32. As discussed in the previous section, the refractive index has to be known or determined independently for this measurement.

Measuring Liquid Fill Height at the Apex and Meniscus Shape Separately

In another embodiment, a fiber-optic interferometer as described in FIGS. 4 and 5 is used to determine the vertical extent of the liquid column at the center of the well.

Light from a light source illuminates the surface through a beam splitter as in the first embodiment depicted in FIG. 1. Light reflected from the sample surface and from a reference surface is made to interfere on a camera or array detector, as in the first embodiment depicted in FIG. 1. The reference surface is positioned in such a way that reference and sample beams interfere on the camera. The image on the camera then shows a pattern of lighter and darker areas, depending on the shape of the liquid meniscus. Lighter areas in the image correspond to areas on the surface of the liquid that are at an elevation such that the optical path length difference between the reference beam and the sample beam is an integer multiple of the wavelength of the illuminating light. Darker areas correspond to areas on the surface of the liquid that are at such an elevation that the optical path length difference between the reference beam and the sample beam is an odd multiple of one half the wavelength of the illuminating light. In this embodiment, the array detector such as a video or line camera acquires an image of this interference pattern and an algorithm is used to calculate the shape of the surface from the interference pattern. The volume of liquid in the well is then calculated from the shape of the surface, the position of the apex of the meniscus relative to the bottom of the well, and the dimensions of the well which can be measured independently as described previously.

What is claimed is:

1. A system for measurement of the fill height of a liquid sample that is held in a container, wherein the liquid sample has a meniscus, the system comprising:
   a low-coherence optical interferometer that is configured to determine the distance to a point on the meniscus of the liquid sample, wherein the container is positioned at a known distance from the interferometer; and
   an analysis unit that is configured to calculate the fill height of the liquid sample in the container based on a difference of the known distance of the container from the interferometer and the determined distance to the point on the meniscus of the liquid sample.

2. The system of claim 1, wherein the analysis unit is further configured to calculate the volume of the liquid sample in the container based on known dimensions of the container and the fill height of the liquid sample in the container.

3. The system of claim 1, wherein the low-coherence optical interferometer comprises a low-coherence Michelson interferometric ranging system (LCMIRS).

4. The system of claim 3, wherein the LCMIRS determines the distance to a point on the meniscus of the liquid sample based on an optical-path-length variation that is effected by a variation of a reference path length of the LCMIRS.

5. The system of claim 3, wherein the LCMIRS determines the distance to a point on the meniscus of the liquid sample based on an optical-path-length variation that is effected by variation of a sample path length of the LCMIRS.

6. The system of claim 3, wherein the LCMIRS comprises optical beams that propagate in open air.

7. The system of claim 3, wherein the LCMIRS comprises optical beams that propagate in optical fibers.

8. The system of claim 7, wherein the LCMIRS determines the distance to a point on the meniscus of the liquid sample based on an optical-path-length variation that is effected by piezo-electric stretching of a portion of the optical fibers.

9. The system of claim 1, wherein the low-coherence optical interferometer comprises a sample beam that is directed at the meniscus from below.

10. The system of claim 1, wherein the container comprises a microplate containing multiple wells.

11. The system of claim 10, wherein the microplate wells are identical.

12. The system of claim 10, wherein the microplate wells vary in size.

13. The system of claim 10, wherein the microplate wells vary in shape.

14. The system of claim 1, further comprising a translation stage that supports the container and is configured to move the container relative to the low-coherence optical interferometer.

15. The system of claim 1, wherein the low-coherence optical interferometer comprises optical beams, and wherein the distance to the meniscus is determined by pixelization of the optical beams.

16. The system of claim 1, wherein the low-coherence optical interferometer comprises a sample beam, and wherein the distance to the meniscus is determined by scanning the sample beam over the meniscus.

17. The system of claim 1, wherein the low-coherence optical interferometer comprises a reference beam and a mirror that reflects the reference beam, and wherein a reflectivity of the mirror is comparable to a reflectivity of the liquid samples.

18. A method of measuring the fill height of a liquid sample that is held in a container, wherein the liquid sample has a meniscus, comprising:
 using a low-coherence optical interferometer to determine the distance to a point on the meniscus of the liquid sample;
 positioning the container at a known distance from the interferometer; and
 calculating the fill height of the liquid sample in the container based on a difference of the known distance of the container from the interferometer and the determined distance to the point on the meniscus of the liquid sample.

19. The method of claim 18, further comprising calculating the volume of the liquid sample in the container based on known dimensions of the container and the fill height of the liquid sample held in the container.

20. The method of claim 18, wherein the meniscus is the boundary between two regions of the liquid sample with different indexes of refraction.

* * * * *